United States Patent
McMorrow

(10) Patent No.: US 9,258,108 B2
(45) Date of Patent: Feb. 9, 2016

(54) CLOSED LOOP, OPTICAL FEEDBACK SYNCHRONIZATION SYSTEM FOR IMAGING APPLICATIONS

(71) Applicant: Gerald McMorrow, Redmond, WA (US)

(72) Inventor: Gerald McMorrow, Redmond, WA (US)

( * ) Notice: Subject to any disclaimer, the term of this patent is extended or adjusted under 35 U.S.C. 154(b) by 130 days.

(21) Appl. No.: 14/223,664

(22) Filed: Mar. 24, 2014

(65) Prior Publication Data

US 2015/0270945 A1   Sep. 24, 2015

(51) Int. Cl.
*G02B 6/00* (2006.01)
*H04L 7/00* (2006.01)
*H04B 10/2581* (2013.01)
*G02B 26/10* (2006.01)
*A61B 1/00* (2006.01)
*A61B 5/00* (2006.01)

(52) U.S. Cl.
CPC .......... *H04L 7/0075* (2013.01); *A61B 1/00172* (2013.01); *G02B 26/103* (2013.01); *H04B 10/2581* (2013.01); *A61B 5/0051* (2013.01); *A61B 5/0062* (2013.01)

(58) Field of Classification Search
CPC .................................................... G02B 26/103
See application file for complete search history.

(56) References Cited

U.S. PATENT DOCUMENTS

2005/0182295 A1*  8/2005  Soper .................. A61B 1/0008
600/117

* cited by examiner

*Primary Examiner* — Uyen Chau N Le
*Assistant Examiner* — Chad Smith
(74) *Attorney, Agent, or Firm* — Foster Pepper PLLC; Richard A. Koske

(57) ABSTRACT

A closed loop, optical feedback synchronization system provides real time feedback and control of a light emitting fiber when scanning or displaying an image. The light emitting fiber is driven by an actuator in an angular pattern to scan the image. Light reflected from a lens assembly is received by an optical synchronizer integrated circuit that includes a slot located between walls of the circuit. The reflected light is directed toward a multi-mode fiber in optical communication with the circuit. A radial position of the reflected light as it passes the slot may be used to compensate for a drift in angular velocity of the light emitting fiber.

19 Claims, 4 Drawing Sheets

CLOSED LOOP, OPTICAL FEEDBACK SYNCHRONIZATION SYSTEM FOR IMAGING APPLICATIONS

FIELD OF THE INVENTION

The present invention generally relates to systems and methods for an optical waveguide feedback or closed loop system that uses reflected light from a lens assembly to determine and control the angular and/or radial position of a scanning fiber.

BACKGROUND

U.S. Pat. No. 6,294,775 describes a minimally invasive, medical, image acquisition having a flexible optical fiber serving as an illuminating wave guide. In one resonance mode, the distal end of the fiber is a stationary node. The fiber includes a lens at the distal tip which collimates emitted light. A scan lens is positioned off the end of the fiber. The relative magnifications and relative positions of the lenses determine the pixel resolution. By way of example, the illumination fiber outputs a light beam or pulse which illuminates a precise spot size. A photon detector detects reflected photons from the object, including the spot. Pixel resolution is determined by the area of the illumination spot (and thus the lens configuration), rather than an area sensed by the detector.

BRIEF SUMMARY OF THE INVENTION

The present invention is generally directed toward a closed loop, optical feedback synchronization system that provides real time feedback and control of a light emitting fiber when scanning an image. The light emitting fiber is driven by an actuator in an angular pattern to scan the image. Light reflected from a lens assembly is received by an optical synchronizer integrated circuit that includes a slot located between walls of the circuit. The reflected light is directed toward a multi-mode fiber in optical communication with the circuit. A radial position of the reflected light as it passes the slot may be used to compensate for a drift in angular velocity of the light emitting fiber.

In one aspect of the present invention, a closed loop, optical feedback synchronization system includes a light source that emits light; a barrel; a lens assembly coupled to the barrel; a single mode fiber for directing the emitted light toward the lens, the single mode fiber having a cantilevered portion extending into the barrel; a driving mechanism for vibrationally deflecting the cantilevered portion of the single mode fiber in accordance with a frequency mode; a multi-mode fiber for receiving light reflected from the lens; a housing; a plurality of conductors extending through the housing; and a synchronizer assembly having a synchronizer body and a synchronizer integrated circuit received in a recess formed in the body, and wherein the synchronizer integrated circuit includes a slot configured to direct the reflected light from the lens assembly to the multi-mode fiber.

In another aspect of the invention, an optical feedback synchronization assembly for stabilizing an imaging operation of an optical imaging device includes a single mode fiber for directing light from a light source toward a lens assembly, the single mode fiber having a cantilevered portion; an actuator for vibrationally deflecting the cantilevered portion of the single mode fiber in accordance with a frequency mode; a multi-mode fiber for receiving light reflected from the lens; and a synchronizer assembly having a synchronizer housing and a synchronizer integrated circuit that is received in a recess formed in the housing, the synchronizer integrated circuit having a slot configured to direct the reflected light from the lens to the multi-mode fiber.

In yet another aspect of the invention, a method for acquiring images using a closed loop, optical feedback synchronization system includes the steps of (1) emitting modulated light from a light source through a single-mode fiber, wherein the light is emitted toward a lens assembly of the optical feedback synchronization system; (2) receiving at least a portion of light reflected from the lens assembly through a slot formed in a synchronizer integrated circuit, wherein in the slot is in optical communication with a multi-mode fiber; (3) determining a radial line of the image based on a position of the reflected light as crosses the slot of the synchronizer integrated circuit; and (4) compensating for a drift in angular velocity of the single-mode fiber by controlling an actuator driving the single-mode fiber.

BRIEF DESCRIPTION OF THE DRAWINGS

Preferred and alternative embodiments of the present invention are described in detail below with reference to the following drawings.

DETAILED DESCRIPTION OF THE INVENTION

In the following description, certain specific details are set forth in order to provide a thorough understanding of various embodiments of the invention. However, one skilled in the art will understand that the invention may be practiced without these details. In other instances, well-known structures associated with display and imaging devices, applications and systems such as, but not limited to scanning fiber endoscope (SFE) systems, optical feedback systems, and optical synchronization systems or assemblies; and methods of operating any of the above have not necessarily been shown or described in detail to avoid unnecessarily obscuring descriptions of the embodiments of the invention.

Presently, single fiber scanning systems, such as those used during medical procedures, operate using an open loop control method. By way of example, the open loop optical imaging systems require periodic calibration, which is typically accomplished by optically scanning a known image and then remapping the image data so that the resulting image sufficiently corresponds to the known image. One drawback of such using such a calibration technique is the need to insure the absolute stability for the mechanical components comprising the system. Variations in temperature, humidity and even handling of the device during or between medical procedures may cause a slow drift that will appear undetected in the images taken between calibrations.

Figure 1:
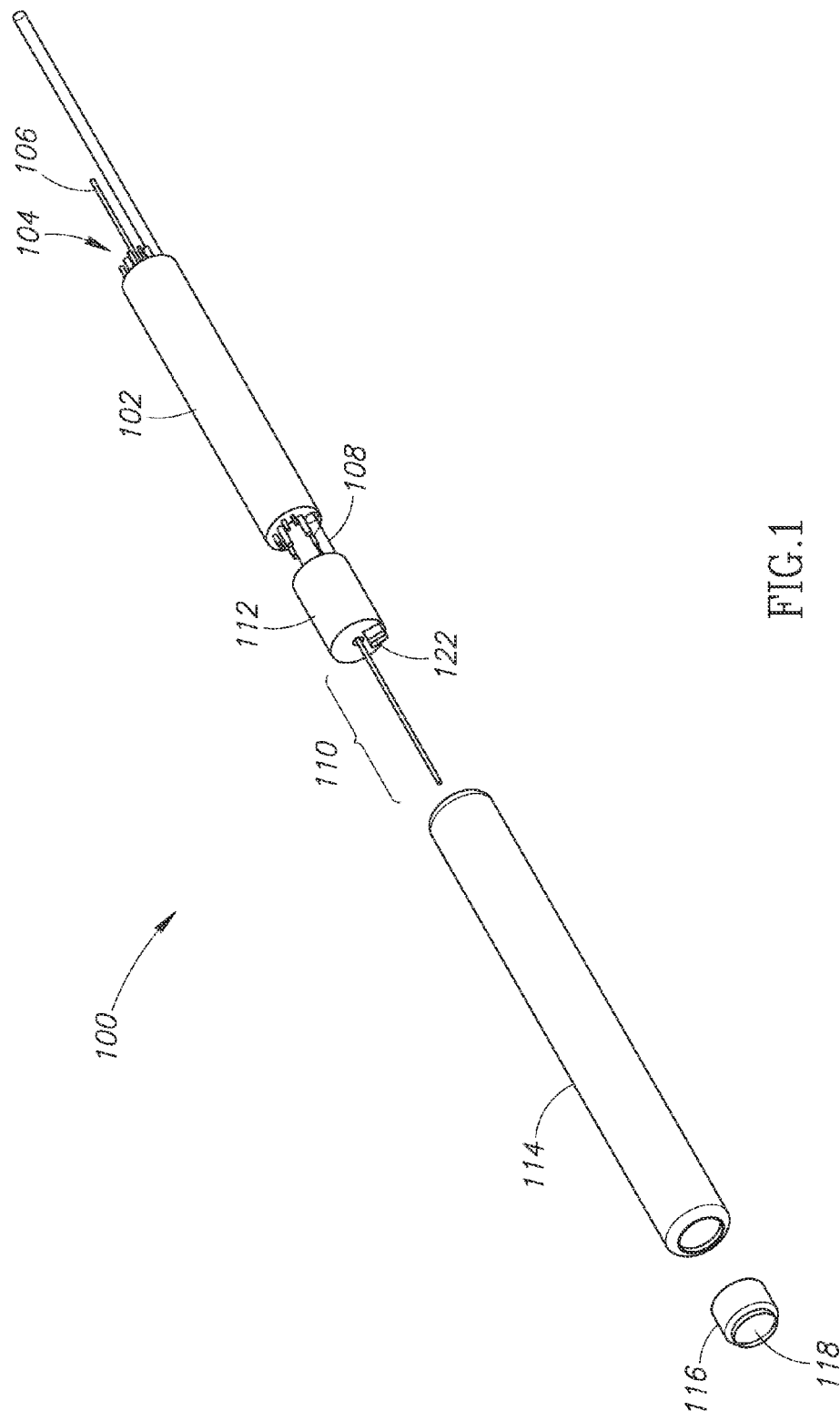
FIG. 1 is a perspective view of a closed loop, optical feedback synchronization system according to an embodiment of the present invention.
Figure 2:
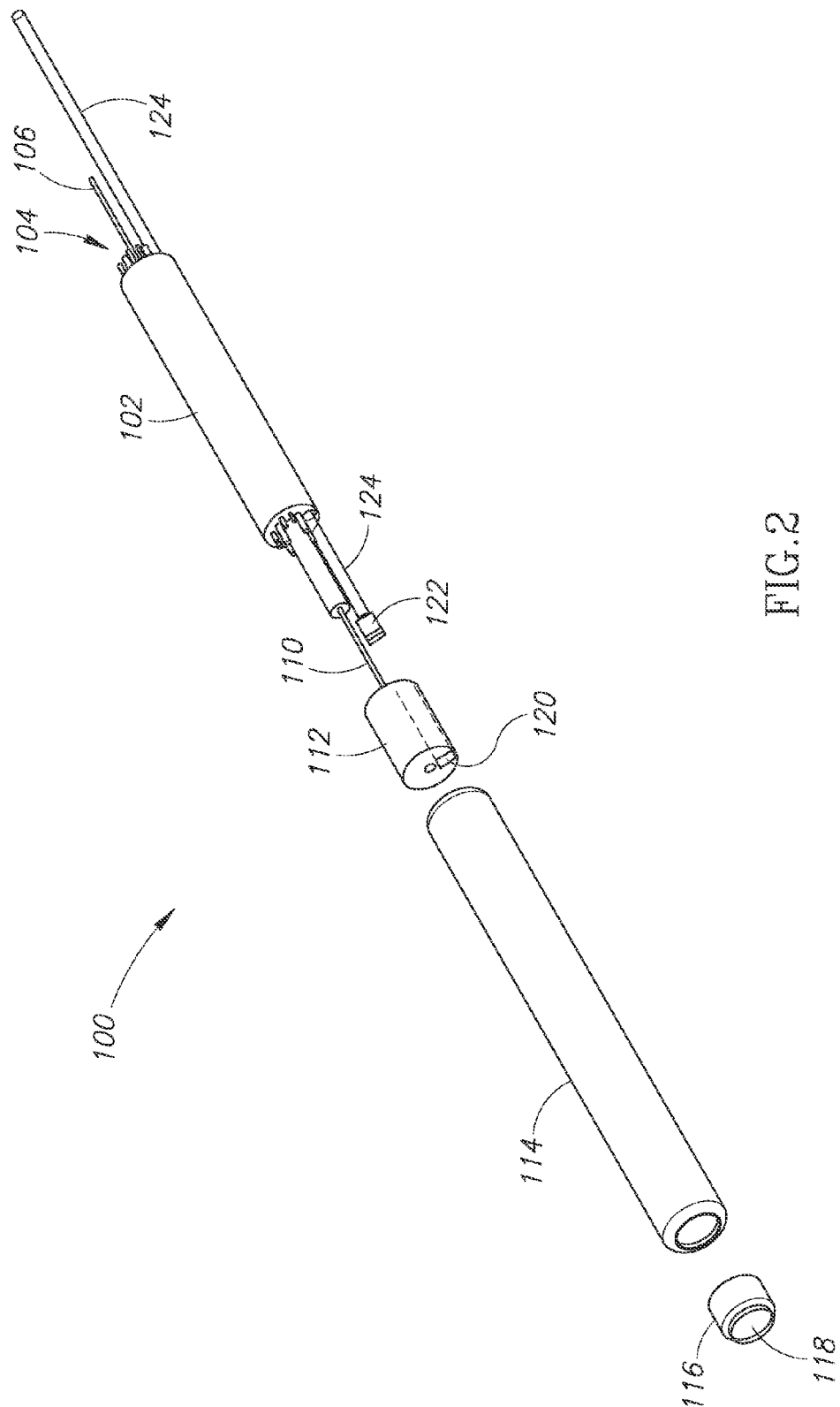
FIG. 2 is an, exploded, perspective view of the closed loop, optical feedback synchronization system of FIG. 1 showing a synchronization optical integrated circuit (i.e., synchronization IC) according to an embodiment of the present invention.

FIGS. 1 and 2 show a closed loop, optical feedback synchronization system 100 that, unlike conventional open loop systems, provides real time feedback of fiber position during use. The optical feedback synchronization system 100, hereinafter referred to as the "synchronization system," includes a housing 102 carrying a plurality of conductors 104 for providing power to an actuator or driving mechanism 108 and to a synchronization integrated circuit (IC) 122. Preferably, the housing 102 is made from an extruded plastic, but it is appreciated that the housing 102 may be made from other non-conductive materials. The synchronization system 100 further includes a single-mode fiber 106 that extends through the housing 102.

The actuator or driving mechanism such as, but not limited to, a piezoelectric actuator is coupled to the housing 102. The actuator 108 provides an anchor point (i.e., fixed from translation or angular movement) for the single-mode fiber 106. The single-mode fiber 106 further includes a cantilevered portion 110 that extends from the actuator 108. The cantilevered portion 110 extends through a synchronization integrated circuit (IC) body or holder 112. The synchronization IC holder 112 will be described in more detail below. The actuator 108 may be driven at a desired frequency mode that provides a vibrational input to the single-mode fiber 106 and may be configured to controllably deflect the cantilevered portion 110 of the single-mode fiber 106 in an angular pattern, a translational pattern, a radial pattern, a circumferential pattern, or some combination thereof. In one embodiment, the desired frequency mode may be close to or equal to a resonant frequency mode for the cantilevered portion 110 of the single-mode fiber 106.

The synchronization system 100 includes a barrel 114 and a lens assembly 116. The barrel 114 provides the structural or physical boundaries for deflection of cantilevered portion 110 of the single-mode fiber 106, which will be explained below regarding the operation of the synchronization system 100. Preferably, the barrel 114 is made from a metallic material such as, but not limited to, Aluminum. The lens assembly 116 includes one or more parasitic reflecting surfaces 118 that reflect light emitted from the single-mode fiber 106. A light source (now shown) that provides the emitted light from the single-mode fiber 106 is preferably a solid state laser diode, but other light generating sources may also be sufficient.

As best shown in FIG. 2, the synchronization IC holder 112 includes a slot or recess 120 that receives the synchronization IC 122. A multi-mode return fiber 124 is coupled to the synchronization IC 122. The multi-mode return fiber 124 receives and transmits light that enters the synchronization IC 122, which will be explained in further detail below. In one embodiment, the multi-mode fiber 124 takes the form of a borosilicate fiber.

Figure 3:
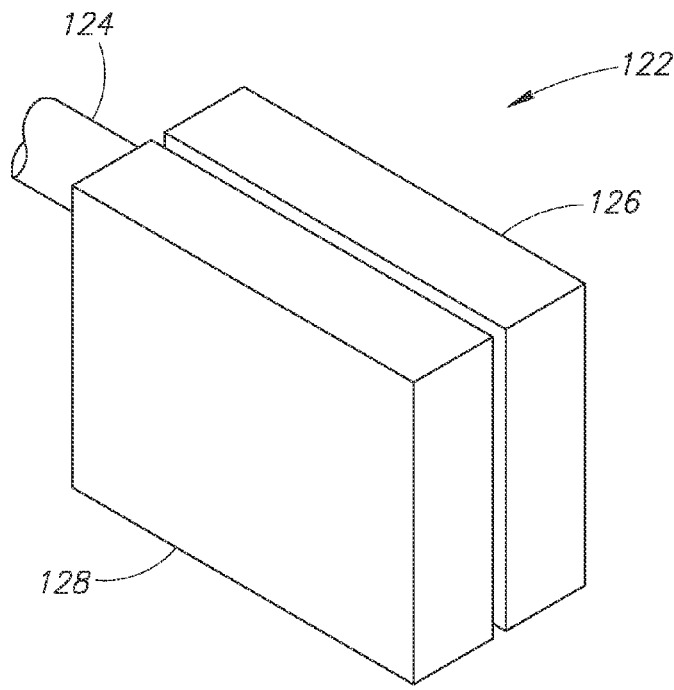
FIG. 3 is a perspective view of a synchronization IC according to an embodiment of the present invention.
Figure 4:
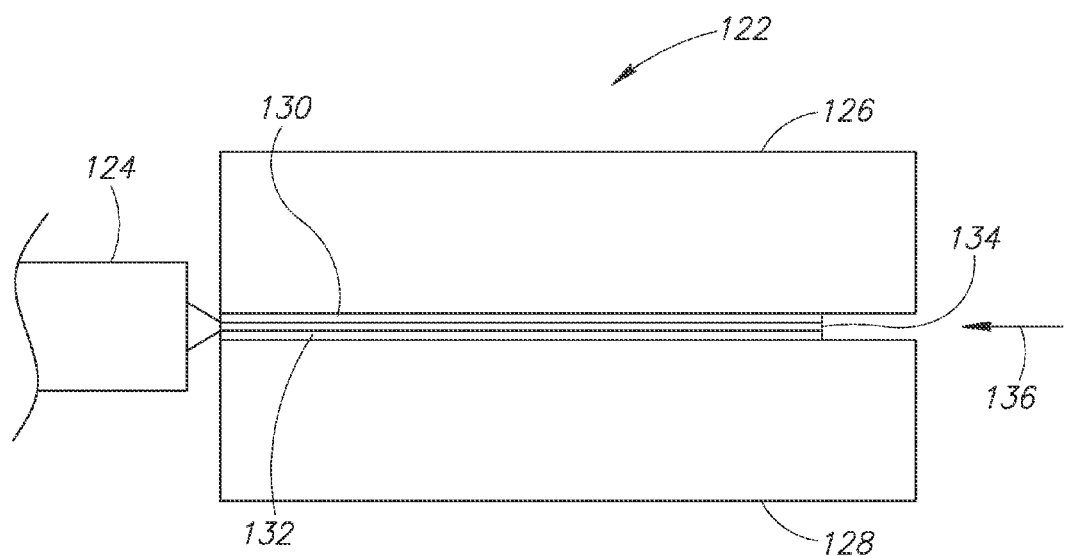
FIG. 4 is a top plan view of a synchronization IC according to an embodiment of the present invention.

FIGS. 3 and 4 show the synchronization IC 122 in optical communication with the multi-mode fiber 124. The synchronization IC 122 includes two walls 126 and 128, respectively. In a preferred embodiment, the walls 126, 128 are made from silicon. As best shown in FIG. 4, the interior surfaces of the walls 126, 128 each have a layer of silicon dioxide 130, 132. A gap or slot 134 is located between the layers 130, 132. The slot 134 receives at least a portion of reflected light 136 from the lens assembly, and then the light 136 travels the length of the slot 134 and enters the multi-mode fiber 124.

Figure 5:
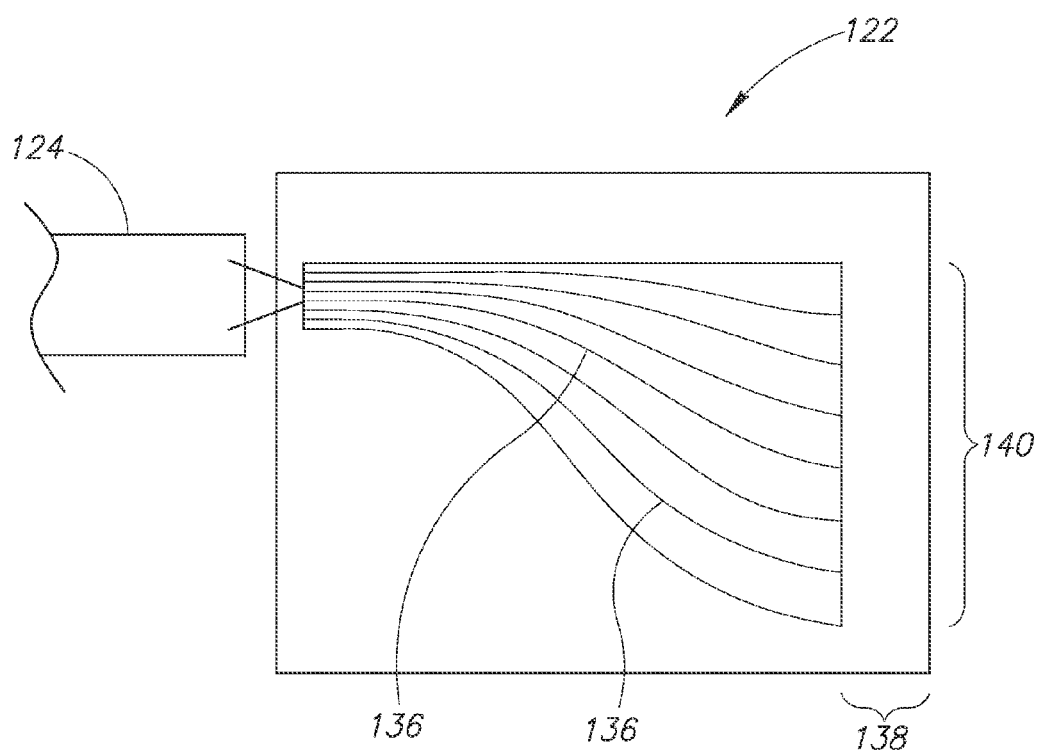
FIG. 5 is a schematic view showing reflected light directed through a synchronization IC and into a multi-mode fiber according to an embodiment of the present invention.

FIG. 5 shows the operation of the optical feedback synchronization system 100. By way of example, the multi-mode fiber 124 senses reflected light 136 from the lens assembly 118 (FIG. 1). The synchronization IC 122 operates as an angular filter and a radial translator of the reflected light 136. Stated otherwise, the synchronization IC 122 allows the optical feedback synchronization system 100 to know when emitted light from the single-mode fiber 106 crosses a known radial line as the system 100 scans an image (not shown). Accordingly, the synchronization IC 122 permits the system 100 to function as a closed loop system, and thus provide feedback to the actuator 108, preferably in real time, to compensate for drift in angular velocity of the cantilevered portion 110 of the single-mode fiber 106, which is driven by the actuator 108. In one embodiment, the synchronization IC 122 may include a setback plane 138 at an entrance 140 of the synchronization IC 122. The setback plane 138 may be selected based on optical simulations of the reflected light 136 from thelens assembly 118. The distance of the setback plane 138 may be varied. The setback plane 138 may advantageously permit the reflected light 136 to form from the lens assembly 118 much like light forms when exiting the single-mode fiber 106.

While the preferred embodiment of the invention has been illustrated and described, as noted above, many changes can be made without departing from the spirit and scope of the invention. In addition, other advantages will also be apparent to those of skill in the art with respect to any of the above-described embodiments whether viewed individually or in some combination thereof. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A closed loop, optical feedback synchronization system comprising:
   a light source that emits light;
   a lens assembly coupled to a barrel;
   a single mode fiber for directing the emitted light toward the lens, the single mode fiber having a cantilevered portion extending into the barrel;
   a driving mechanism for vibrationally deflecting the cantilevered portion of the single mode fiber in accordance with a frequency mode;
   a multi-mode fiber for receiving light reflected from the lens;
   a housing;
   a plurality of conductors extending through the housing; and
   a synchronizer assembly having a synchronizer body and a synchronizer integrated circuit received in a recess formed in the body, and wherein the synchronizer integrated circuit includes a slot configured to direct the reflected light from the lens assembly to the multi-mode fiber.

2. The system of claim 1, wherein the frequency mode is a resonant frequency mode of the cantilevered portion of the single mode fiber.

3. The system of claim 1, wherein the lens assembly includes one or more parasitic reflectors.

4. The system of claim 1, wherein the driving mechanism is a piezoelectric actuator.

5. The system of claim 1, wherein the connectors are configured to be in electrical communication with the driving mechanism and the synchronizer integrated circuit.

6. The system of claim 1, wherein walls of the synchronizer integrated circuit are made from silicon and an interior surface of one or more walls includes a layer of silicon dioxide.

7. The system of claim 1, wherein the slot of the synchronizer integrated circuit is located on a silicon dioxide layer.

8. The system of claim 1, wherein synchronizer integrated circuit includes a setback plane at an entrance of the circuit.

9. An optical feedback synchronization assembly for stabilizing an imaging operation of an optical imaging device, the assembly comprising:
   a single mode fiber for directing light from a light source toward a lens assembly, the single mode fiber having a cantilevered portion;
   an actuator for vibrationally deflecting the cantilevered portion of the single mode fiber in accordance with a frequency mode;
   a multi-mode fiber for receiving light reflected from the lens; and
   a synchronizer assembly having a synchronizer housing and a synchronizer integrated circuit that is received in a recess formed in the housing, the synchronizer integrated circuit having a slot configured to direct the reflected light from the lens to the multi-mode fiber.

10. The assembly of claim 9, wherein the frequency mode is a resonant frequency mode.

11. The assembly of claim 9, wherein the actuator is a piezoelectric actuator.

12. The assembly of claim 9, wherein walls of the synchronizer integrated circuit are made from silicon and an interior surface of each wall includes a layer of silicon dioxide.

13. The assembly of claim 12, wherein the slot of the synchronizer integrated circuit is located between the silicon dioxide layers.

14. The assembly of claim 9, wherein the multi-mode fiber is a borosilicate fiber.

15. The assembly of claim 9, wherein synchronizer integrated circuit includes a setback plane at an entrance of the circuit.

16. A method for acquiring images using a closed loop, optical feedback synchronization system, the method comprising:
   emitting modulated light from a light source through a single-mode fiber, wherein the light is emitted toward a lens assembly of the optical feedback synchronization system;
   receiving at least a portion of light reflected from the lens assembly through a slot formed in a synchronizer integrated circuit, wherein the slot is in optical communication with a multi-mode fiber;
   determining a radial line of the image based on a position of the reflected light as crosses the slot of the synchronizer integrated circuit; and
   compensating for a drift in angular velocity of the single-mode fiber by controlling an actuator driving the single-mode fiber.

17. The method of claim 16, wherein controlling the actuator includes controlling a piezoelectric actuator.

18. The method of claim 17, further comprising driving the piezoelectric actuator at a resonant frequency of a cantilevered portion of the single-mode fiber coupled to the actuator.

19. A closed loop, optical feedback synchronization system comprising:
   a light source that emits modulated light carrying an image to be displayed on a surface;
   a lens assembly coupled to a barrel;
   a single mode fiber for directing the emitted light toward the lens, the single mode fiber having a cantilevered portion extending into the barrel;
   a driving mechanism for vibrationally deflecting the cantilevered portion of the single mode fiber in accordance with a frequency mode;
   a multi-mode fiber for receiving light reflected from the lens assembly;
   a housing;
   a plurality of conductors extending through the housing; and
   a synchronizer assembly having a synchronizer body and a synchronizer integrated circuit received in a recess formed in the body, and wherein the synchronizer integrated circuit includes a slot configured to direct the reflected light from the lens assembly to the multi-mode fiber.

* * * * *